US009956375B2

(12) United States Patent
McNew

(10) Patent No.: US 9,956,375 B2
(45) Date of Patent: May 1, 2018

(54) LIGHT AND SOUND THERAPY DEVICE

(71) Applicant: Barry McNew, Pretty Prairie, KS (US)

(72) Inventor: Barry McNew, Pretty Prairie, KS (US)

( * ) Notice: Subject to any disclaimer, the term of this patent is extended or adjusted under 35 U.S.C. 154(b) by 246 days.

(21) Appl. No.: 14/951,336

(22) Filed: Nov. 24, 2015

(65) Prior Publication Data

US 2016/0144151 A1  May 26, 2016

Related U.S. Application Data

(60) Provisional application No. 62/123,626, filed on Nov. 24, 2014.

(51) Int. Cl.
*A61M 21/02* (2006.01)
*A61M 21/00* (2006.01)

(52) U.S. Cl.
CPC ........ *A61M 21/02* (2013.01); *A61M 21/0094* (2013.01); *A61M 2021/0022* (2013.01); *A61M 2021/0027* (2013.01); *A61M 2021/0044* (2013.01); *A61M 2205/053* (2013.01); *A61M 2205/332* (2013.01); *A61M 2205/3375* (2013.01); *A61M 2205/502* (2013.01); *A61M 2205/584* (2013.01)

(58) Field of Classification Search
CPC .. A61N 5/06; A61N 5/0614; A61N 2005/064; A61N 2005/0661; A61N 5/0613; A61N 5/0616; A61N 2005/0615; A61N 2005/0633; A61G 11/00; A61G 11/009; A61G 2203/46; A61G 11/002; A61G 11/005; A61G 11/006
See application file for complete search history.

(56) References Cited

U.S. PATENT DOCUMENTS

| | | | |
|---|---|---|---|
| 4,640,266 A | 2/1987 | Levy | |
| 5,676,633 A | 10/1997 | August | |
| 5,891,186 A * | 4/1999 | Daffer | A61H 23/02 600/21 |
| 6,544,165 B1 | 4/2003 | McNew | |
| 7,108,654 B2 | 9/2006 | McNew | |
| 7,141,028 B2 | 11/2006 | McNew | |
| 7,578,783 B2 | 8/2009 | Klein | |
| 7,654,949 B2 | 2/2010 | McNew | |
| 7,815,668 B2 | 10/2010 | Butler | |
| 7,846,086 B2 | 12/2010 | McNew | |
| 8,337,385 B1 | 12/2012 | Cornell | |
| 2003/0191359 A1* | 10/2003 | McNew | A61M 21/0094 600/27 |
| 2009/0005838 A1* | 1/2009 | Wagenaar-Cacciola | A61N 5/0614 607/91 |
| 2010/0298627 A1 | 11/2010 | Berezhkov | |
| 2013/0071829 A1 | 3/2013 | Berezhkov | |

* cited by examiner

*Primary Examiner* — Christine H Matthews
(74) *Attorney, Agent, or Firm* — John A. Arsenault; Daniel Dubuisson

(57) ABSTRACT

A device and method for administering light and acoustic vibrations for therapeutic treatment of one or more users is disclosed. The device has acoustic transducers positioned along a longitudinal center plane and comprises two longitudinal side sections that take an elliptical segment form. The acoustic transducers direct acoustic vibrations upwards, and the device also has light fixtures that direct light downward in the device interior. The components of the device work together to provide auditory, ocular, and dermal stimulation with a substantial reduction in undesirable rattling and echo.

16 Claims, 4 Drawing Sheets

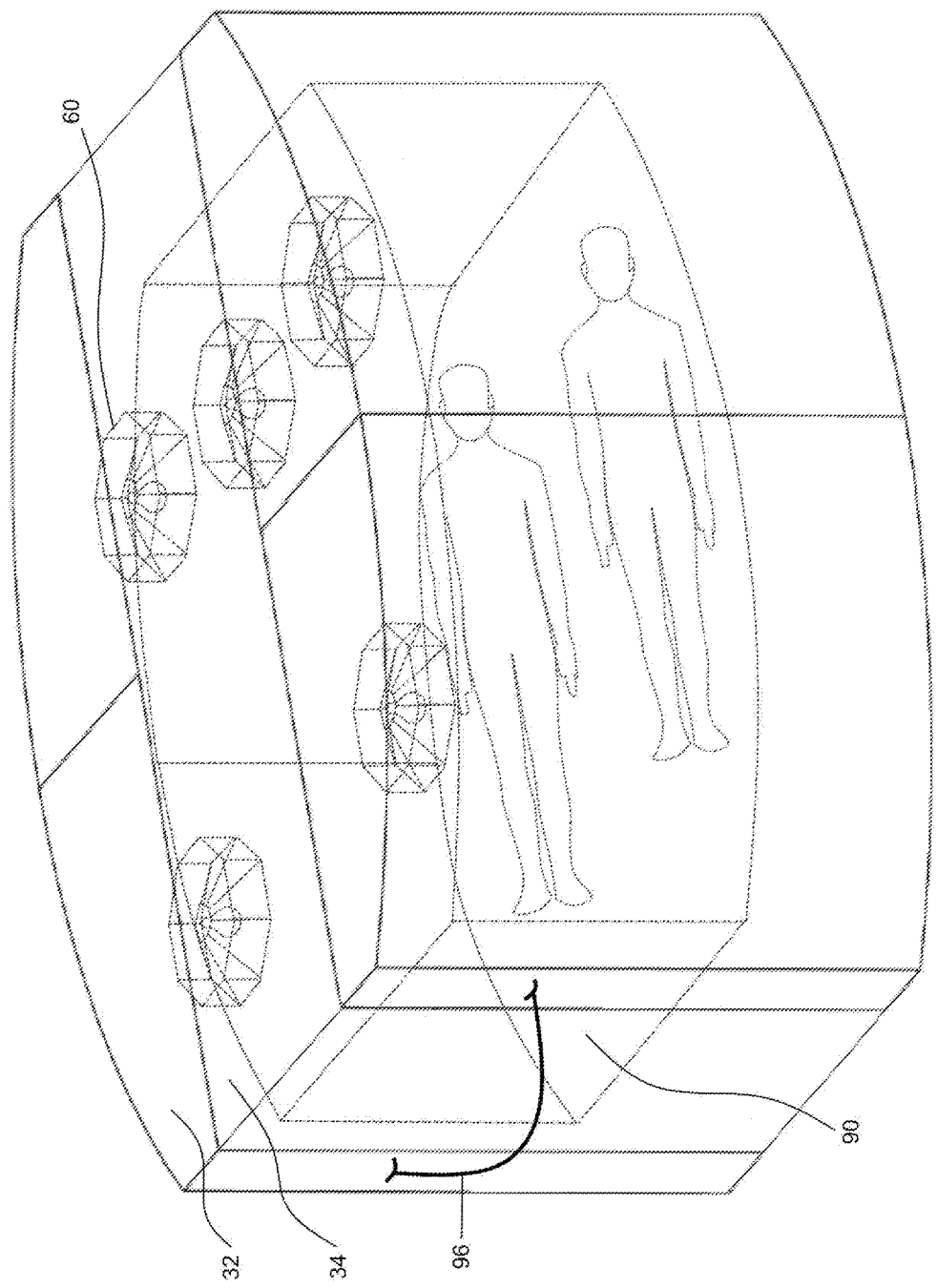

LIGHT AND SOUND THERAPY DEVICE

STATEMENT REGARDING FEDERALLY SPONSORED RESEARCH AND DEVELOPMENT

Not Applicable.

CROSS-REFERENCE TO RELATED APPLICATIONS

This application is related to and/or claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)). In addition, the present application is related to the "Related Applications," if any, listed below.

PRIORITY APPLICATIONS

U.S. Provisional Patent Application App. No. 62/123,626 titled "Energy Genesis," filed on Nov. 24, 2014, the subject matter of which is incorporated by reference herein in its entirety.

If the listings of applications provided above are inconsistent with the listings provided via an ADS, it is the intent of the Applicant to claim priority to each application that appears in the Priority Applications section of the ADS and to each application that appears in the Priority Applications section of this application.

All subject matter of the Priority Applications and the Related Applications and of any and all parent, grandparent, great-grandparent, etc. applications of the Priority Applications and the Related Applications, including any priority claims, is incorporated herein by reference to the extent such subject matter is not inconsistent herewith.

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

BACKGROUND OF DISCLOSURE

1. Field of Invention

The present invention generally relates to therapeutic devices and more particularly relates to a device and method for applying acoustic vibration and light for therapeutic treatment of one or more users.

2. Description of Prior Art

Enclosures that apply acoustic and light for therapeutic benefit to a user lying within are popular amongst children and adults. Numerous acoustic and light enclosures are well known but all suffer from significant disadvantages. U.S. Pat. No. 7,578,783 to Klein discloses a method and apparatus for stimulating a user, whereby a user floats in a pool of liquid and is exposed to acoustic, light, and essential oils that are directed to the atmosphere above the user. U.S. Pat. No. 8,337,385 to Cornell discloses a cabinet with a base section having speakers, a middle section for accommodating a user, and an upper section having light fixtures that emit light at preselected frequencies that relate to the acoustic frequencies generated by the speakers.

The prior art describes acoustic and light enclosures for relaxing or therapeutically treating a user; however, various components of the prior art devices, such as the enclosure doors or entryways, are prone to undesirable rattling caused by the acoustics produced within. Furthermore, the prior art devices are not designed or intended to stimulate multiple users simultaneously. The present invention overcomes these disadvantages by incorporating speakers into the doorway components so that a user is therapeutically treated with the acoustic that would cause rattling in the prior art devices. The doorways of the present invention also incorporate an elliptical segment shape to further reduce rattling while enhancing the quality of acoustic vibrations. Additionally, the present invention has manufacturing advantages over the prior art and is designed to be more portable and able to be shipped in parts and assembled at the location desired for use.

SUMMARY OF THE DISCLOSURE

The present invention provides an improved light and sound therapy device and method capable of stimulating or relaxing one or more users.

In a preferred embodiment, the light and sound therapy device comprises a longitudinal center section having a center lower structure, a center upper structure, a transverse head section, and a transverse feet section, wherein the center lower structure has one or more acoustic transducers positioned along a longitudinal center plane and directed towards the center upper structure, wherein the center upper structure comprises one or more light fixtures positioned along the longitudinal center plane and directing light towards the center lower structure. The device further comprises two longitudinal side sections, each having two longitudinal subsections, wherein each longitudinal subsection has a side upper structure, a side lower structure, and a side wall. At least one of the longitudinal subsections is releasably adjoined substantially near a transverse center plane to another of the longitudinal subsections of one of the longitudinal side sections and is hinged to the transverse head section or the transverse feet section.

In an embodiment, the acoustic and light therapy device further comprising one or more comfort pads for enhancing user comfort and reducing rattling, wherein the comfort pads are positioned directly above one or more of the center lower structure and the side lower structure. In an embodiment, the comfort pad is comprised of a comfort pad center section and one or more comfort pad side sections as one component. In an embodiment, the comfort pad further comprises a weight sensor pad for determining the weight distribution of a user on the comfort pad over a duration of time.

In an embodiment, one or more longitudinal side sections takes a form of an elliptical segment for enhancing acoustic vibration quality. In an embodiment, one or more light fixtures are in the form of a polyhedral section comprising a plurality of mirrors for directing light towards the side lower structure or the center lower structure. In an embodiment, the form of polyhedral section is radially symmetric about a light fixture center.

In an embodiment, one or more longitudinal subsections further comprise one or more acoustic transducers positioned on the side lower structure and directed towards one of the side upper structures.

In an embodiment, one or more longitudinal subsection(s) further comprise one or more light fixtures positioned on the side upper structure and directed towards one of the side lower structures.

In an embodiment, the acoustic and light therapy device further comprises at least one control knob for adjusting intensity of acoustic vibration, one control knob for adjusting intensity of light, or at least one frequency selective control for adjusting intensity of acoustic vibration within a range of frequencies.

In an embodiment, at least one of the longitudinal subsections are mirrored about the transverse center plane. In another embodiment, at least one of the longitudinal side sections, transverse head section, or transverse feet section comprises a non-allergenic material, pine or another generally soft wood.

In an embodiment, at least one light fixture further comprises a light filter for reducing electromagnetic radiation intensity in selective ranges. In an embodiment, the center upper structure further comprises an ultraviolet emitter for disinfecting the device interior. In an embodiment, at least one light fixture comprises a color distribution for enhancing comfort to a user.

In a preferred embodiment, the method for applying acoustic and light therapy to one or more users generally comprises the steps of supporting a user on a comfort pad positioned above one or more acoustic transducers secured directly onto a center lower structure and along a longitudinal center plane, generating acoustic vibration at the acoustic transducers, directing the acoustic vibration towards a center upper structure, and generating light at one or more light fixtures secured directly to the center upper structure, and directing the light towards the center lower structure. The method is safe, noninvasive, nontoxic, and accommodates users of various ages and sizes.

In embodiments, the method may further comprise one or a combination of the steps of generating acoustic vibration at one or more acoustic transducers secured directly onto a side lower structure, directing the acoustic vibration towards a side upper structure, generating light at one or more light fixtures secured directly to a side upper structure, directing the light towards a side lower structure, and adjusting intensity of acoustic vibration or light generated via one or more control knobs.

The acoustic and light therapy device exhibits synergistic effects while in operation with two users; however it also works effectively with one user. The light fixtures and acoustic transducers may be sequenced to alter intensities generated about different parts of the chamber at desired times. The device may take an open configuration whereby the longitudinal subsections act as doorways; in a closed configuration, the device is symmetric about a longitudinal center plane.

Embodiments include one, more, or any combination of all of the features listed above.

Other features and advantages of the present invention will become apparent from the following more detailed description, taken in conjunction with the accompanying, which illustrate, by way of example, the principles of the invention.

DESCRIPTION OF THE DRAWINGS

FIG. 3a and FIG. 3b are top views of the acoustic and light therapy device, wherein FIG. 3a is the acoustic and light therapy device in an open configuration, and wherein FIG. 3b is the acoustic and light therapy device in a closed configuration, in accordance with an exemplary embodiment of the present invention;

FIG. 9 is a perspective view of an acoustic and light therapy device showing two users laying on a comfort pad and preparing to receive therapeutic treatment, in accordance with an exemplary embodiment of the present invention.

Figure 1:
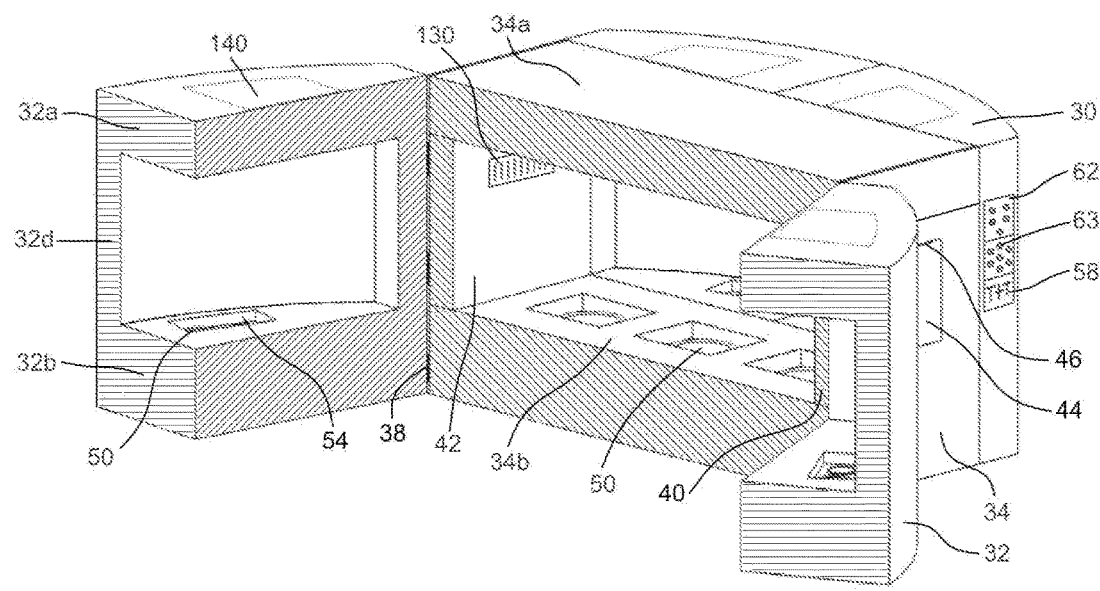
FIG. 1 is an elevated perspective view of the acoustic and light therapy device in an open configuration displaying acoustic transducers, in accordance with an exemplary embodiment of the present invention.

REFERENCE NUMERALS IN THE DRAWINGS longitudinal side section 30
longitudinal subsection 32
side upper structure 32a
side lower structure 32b
side wall 32d
longitudinal center section 34
center upper structure 34a
center lower structure 34b
hinges 38
transverse head section 40
transverse feet section 42
head access door 44
viewing slot 46
acoustic transducer 50
acoustic transducer enclosure 50b
acoustic gap 54
frequency selective control 58
light fixture 60
color distribution 61
control panel 62
control knob 63
light filter 64
light source 66
mirror 68
ultraviolet emitter 69
comfort pad 90
comfort pad center section 90a
comfort pad side subsection 90b
wire pull 96
signal button 128
vent 130
removable panel 140 longitudinal center plane 200
transverse center plane 210

DETAILED DESCRIPTION OF THE DISCLOSED EMBODIMENT

Illustrative embodiments of the invention are described below in the accompanying Figures. The following detailed description provides detailed schematics for a thorough understanding of and an enabling description for these embodiments. One having ordinary skill in the art will understand that the invention may be practiced without certain details. In other instances, well-known structures and functions have not been shown or described in detail to avoid unnecessarily obscuring the description of the embodiments.

FIG. 1 is an elevated perspective view of an acoustic and light therapy device in an open configuration displaying acoustic transducers 50, in accordance with an exemplary embodiment of the present invention. The example device shown in FIG. 1 comprises a longitudinal center section 34 and two longitudinal side sections 30. The longitudinal center section 34 comprises a center lower structure 34b, a center upper structure 34a, a transverse head section 40, and a transverse feet section 42. The longitudinal side sections 30 each comprise two longitudinal subsections 32, wherein each longitudinal subsection 32 comprises a side upper structure 32a, a side lower structure 32b, and a side wall 32d. At least one of the longitudinal side sections 30 comprises at least one pair of longitudinal subsections 32 releasably adjoined substantially near the transverse center plane 210, wherein the releasably adjoined subsections are hinged via a plurality of hinges 38 to either the transverse head section 40 or the transverse feet section 42, thus allowing one or more users to open the device, enter the interior volume, and close the device, as desired. The center lower structure 34b comprises one or more acoustic transducers 50 positioned on the upper surface and along the longitudinal center plane 200 and directed towards the center upper structure 34a. Each longitudinal subsection 32 may also comprise one or more acoustic transducers 50 positioned on the upper surface of the lower structure 32b and each directed towards the corresponding side upper structure 32a. Prior to operation, a comfort pad 90 is generally positioned directly above the acoustic transducers 50 and covers the upper surface of lower structures 32b and 34b. In an embodiment, an acoustic gap 54 or volume of air is situated between the comfort pad 90 and acoustic transducer 50 to enhance the quality of acoustic vibrations within the device. A vent 130 positioned on the interior surface of the transverse feet section 42 communicates and circulates air to and from the exterior of the device. In an embodiment, an upper edge of the center upper structure 34a is hinged to the upper longitudinal edge of a longitudinal section 30 via hinges 38 to allow the center upper structure 34a to be raised by a user while in the open configuration.

The acoustic and light therapy device generally comprises a control panel 62 having one or more control knobs 63 for allowing a user or operator to change the intensity of acoustic vibration or the intensity of light of individual components as desired. In an embodiment, the control panel 62 may further comprise one or more frequency selective controls 58, such as a multi-band parametric or graphic equalizer, that allow a user to adjust the intensity of acoustic vibration or light within a desired range of frequencies.

Figure 2:
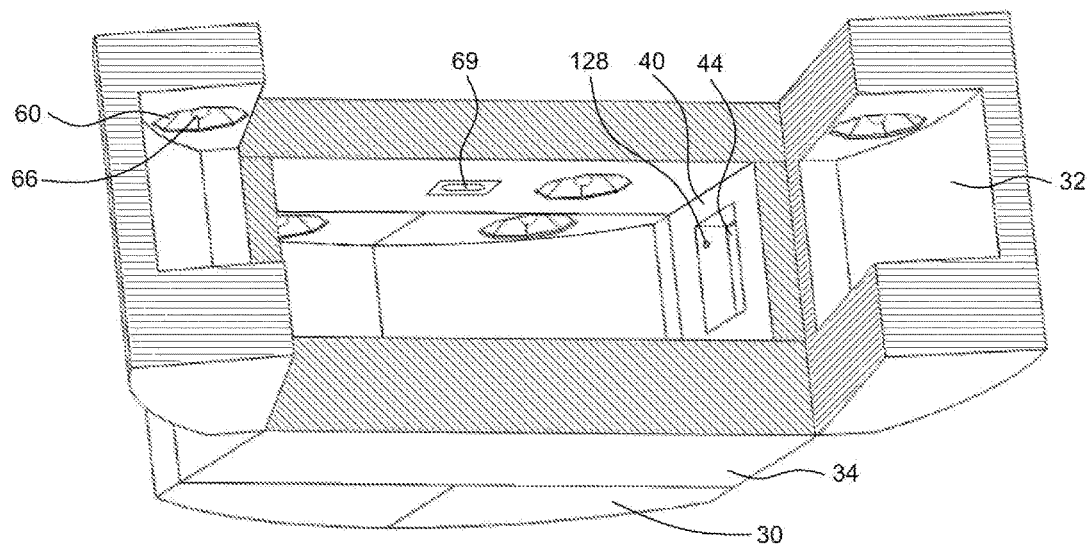
FIG. 2 is a lowered perspective view of the acoustic and light therapy device of FIG. 1 in an open configuration displaying light fixtures, in accordance with an exemplary embodiment of the present invention.

FIG. 2 is a lowered perspective view of the acoustic and light therapy device of FIG. 1 in an open configuration displaying light fixtures 60, in accordance with an exemplary embodiment of the present invention. The center upper structure 34 comprises one or more light fixtures 60 positioned along the longitudinal center plane 200 and comprises a light source 66 directed towards the center lower structure 34b. Each longitudinal subsection 32 may also comprise one or more light fixtures 60 positioned on the lower surface of the corresponding side upper structure 32a and each directed towards the corresponding side lower structure 32b.

The example embodiment in FIG. 1 and FIG. 2 shows the control panel 62 positioned on the exterior side of the transverse head section 40 adjacent to a viewer slot 46. During operation or while making adjustments, the environment outside of the device is kept substantially darker than the interior, thus allowing a user on the exterior to view and monitor a user or the environment within. In some cases, such as when one of the users is a child, it is beneficial that the transverse head section 40 further comprise a head access door 44 for enabling a parent to insert a child into the device in an alternative manner while it is in a closed configuration. It is a further embodiment for the acoustic and light therapy device to comprise a signal button 128 located on any surface of the interior for enabling a user within the device to signal to the exterior for assistance. Types of signals emitted upon pressing the signal button 128 include, but are not limited to, a chime, an alarm, a bell, a light, a buzzer, or a tone.

In an embodiment, the device may further comprise an ultraviolet emitter 69 for disinfecting the interior of the device, wherein the ultraviolet emitter 69 generates and directs germicidal ultraviolet radiation towards the surfaces of the interior at times when the interior is vacant of a user, thus reducing the passing of bacteria, viruses, and other pathogens between users. Example ultraviolet emitters 69 are low pressure mercury vapor lamps, amalgam lamps, medium pressure lamps, and low ozone lamps, although it is contemplated that other ultraviolet emitters 69 may suffice. In the example embodiment of FIG. 2, the ultraviolet emitter 69 is positioned along the lower surface of the center upper structure 34a and activates via a control knob 63 on the control panel 62.

Figure 3A:
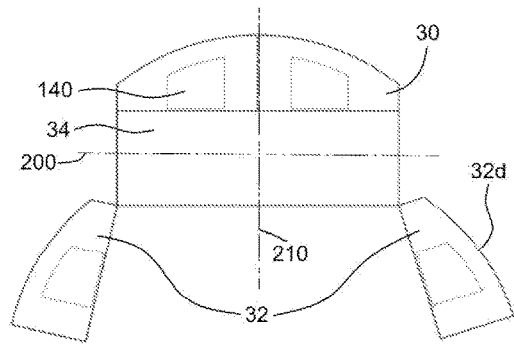
Figure 3B:
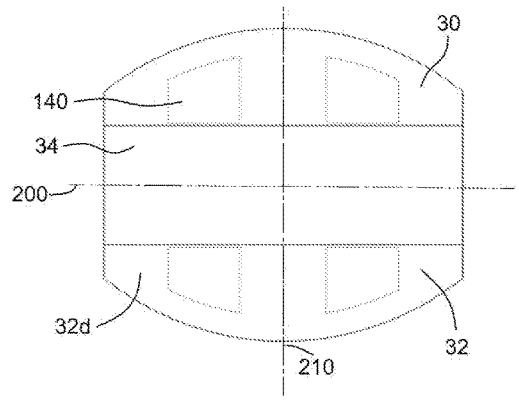

FIG. 3a and FIG. 3b are top views of the acoustic and light therapy device, wherein FIG. 3a is the acoustic and light therapy device in an open configuration, and wherein FIG. 3b is the acoustic and light therapy device in a closed configuration, in accordance with an exemplary embodiment of the present invention. The side walls 32d of the longitudinal subsections 32 are curved with the greatest distance between longitudinal side sections 30 being located substantially near the transverse center plane 210 so that one or more of said longitudinal side sections assumes, at least in part, an elliptical segment form. The elliptic form characteristics of the device provides several advantages over the prior art, such as enhanced propagation of acoustic vibration. The upper portion of each side upper structures 32a with a light fixture 60 generally comprises a removable panel 140 to enhance the ability of a user to replace or perform maintenance on light fixtures 60 in a time efficient manner. In a closed configuration, the structural components of the device are symmetric about both the longitudinal center plane 200 and the transverse center plane 210.

Figure 4:
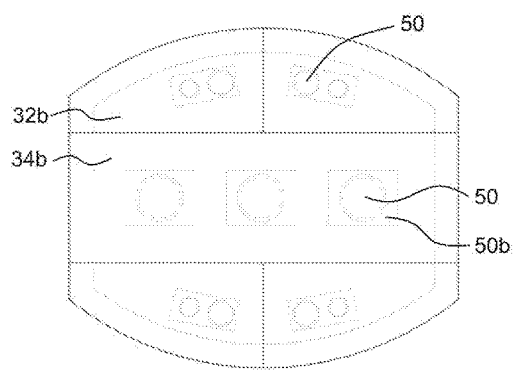
FIG. 4 is a top view of lower structures of the acoustic and light therapy device of FIG. 1 and FIG. 2 in a closed configuration showing a general arrangement of the acoustic transducers, in accordance with an exemplary embodiment of the present invention.

FIG. 4 is a top view of lower structures 34b and 32b of the acoustic and light therapy device of FIG. 1 and FIG. 2 in a closed configuration showing a general arrangement of the acoustic transducers 50, in accordance with an exemplary embodiment of the present invention. Acoustic transducers 50 positioned along the longitudinal center plane 200 are generally designed to efficiently generate lower frequency acoustic vibration in the range of 10 to 250 hertz and are directed towards the volume between two users or at the spine of a single user. The lower frequency acoustic vibration is capable of penetrating the body of a user and resonating and stimulating the nervous system and selective organs of the user. Acoustic transducers 50 positioned in one or more of the longitudinal side sections 30 are generally designed to generate acoustic vibration in the frequency range of 100 to 20,000 hertz and are directed towards the sides of one or more users; however, it is contemplated that one or more acoustic transducers 50 in longitudinal side sections 30 may emit lower frequencies to further enhance performance of the device. In some cases, it may be desirable for one or more acoustic transducers 50 to be mounted onto an acoustic transducer enclosure 50b, which may be in the form of a sealed enclosure, a ported enclosure, or a bandpass enclosure. Changes in the amplitude of acoustic vibration are generally performed via a control knob 63 on the control panel 62. In an embodiment, the center lower structure 34b comprises three acoustic transducers 50 positioned along the longitudinal center plane 200, wherein one of the acoustic transducers 50 is positioned substantially near the transverse center plane 210 and controlled by a control knob 63, and the other two acoustic transducers 50 are positioned one each side of the transverse center plane 210 and are controlled by a second control knob 63.

Figure 5:
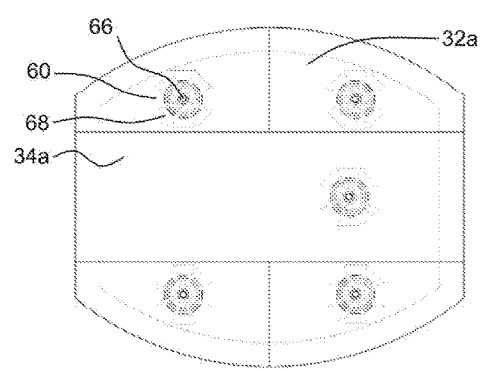
FIG. 5 is a bottom view of upper structures of the acoustic and light therapy device of FIG. 4 in a closed configuration showing a general arrangement of the light fixtures, in accordance with an exemplary embodiment of the present invention.

FIG. 5 is a bottom view of upper structures 34a and 32a of the acoustic and light therapy device of FIG. 4 in a closed configuration showing a general arrangement of the light fixtures 60, in accordance with an exemplary embodiment of the present invention.

Figure 6:
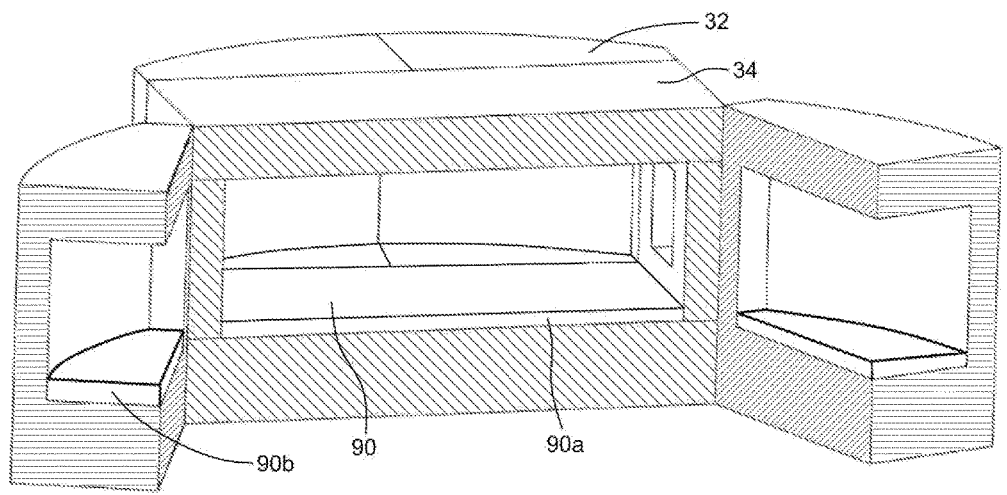
FIG. 6 is an elevated perspective view of the acoustic and light therapy device in an open configuration, in accordance with an exemplary embodiment of the present invention.

FIG. 6 is an elevated perspective view of the acoustic and light therapy device in an open configuration, in accordance with an exemplary embodiment of the present invention. The comfort pad 90 generally comprises a porous or padded material to provide enhanced comfort to the user and to disperse acoustic vibration from the acoustic transducers 50 in the lateral directions. In an embodiment, the comfort pad 90 further comprises a weight sensor pad for determining the weight distribution of a user on the comfort pad 90 over a duration of time. Examples of weight sensor pads that would suffice include, but are not limited to, a diode sensor pad comprising a plurality of diodes, force gauge pad, and pressure gauge pad. Information about the weight distribution may be collected and stored in a processor, then output to a display monitor positioned on an interior or exterior surface of the device. In an embodiment, the interior surfaces of the side walls 32d, transverse head section 40, or transverse feet section 42 may comprise a plurality of vertically aligned indentations for further reducing echo and rattling. In an embodiment, the comfort pad 90 is comprised of a comfort pad center section 90a and one or more comfort pad side sections 90b as one component.

Figure 7:
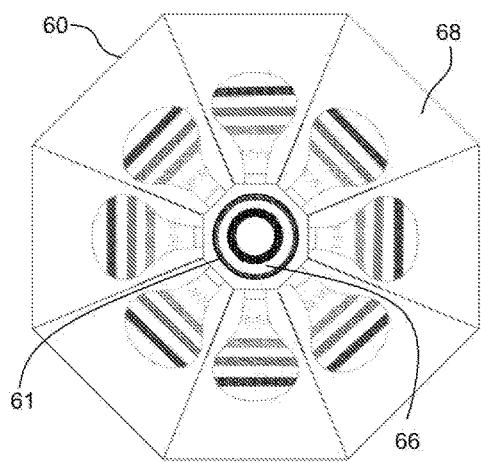
FIG. 7 is a bottom view of a light fixture, in accordance with an exemplary embodiment of the present invention.

FIG. 7 is a bottom view of a light fixture, in accordance with an exemplary embodiment of the present invention. The light source 66 may further comprise a color distribution 61 for enhancing user ocular or dermal stimulation. In an embodiment, the light fixture 60 further comprises a plurality of mirrors 68 for redirecting light and color distributions 61 in a pattern that is stimulating to the user. In an embodiment, the light fixture 60 takes a form of a polyhedral section symmetric about the light source 66.

Figure 8:
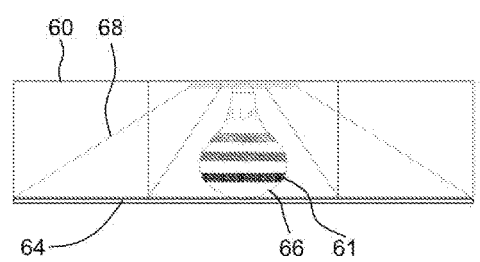
FIG. 8 is a side view of a light fixture, in accordance with an exemplary embodiment of the present invention.

FIG. 8 is a side view of a light fixture, in accordance with an exemplary embodiment of the present invention. The light fixtures 60 may comprise an LED or a lamp capable of emitting electromagnetic radiation with 400 to 700 nanometer wavelengths and may further comprise a light filter 64 for reducing selective ranges of electromagnetic radiation from emitting towards a user in the device interior. The light filter 64 may comprise glass, quartz, a polymeric material, a material exhibiting at least partial opacity in the infrared, light, or ultraviolet frequency ranges, or any combination thereof.

FIG. 9 is a perspective view of the acoustic and light therapy device showing two users laying on a comfort pad and preparing to receive therapeutic treatment, in accordance with an exemplary embodiment of the present invention. The large volume of air in the interior of the device enhances both the comfort of the users during operation and the transmission of low frequency acoustic vibration to the users. The acoustic and light therapy device may further comprise wheels positioned on the lower portion of any one of lower structures 32b and 34b and a wire pull 96 positioned on the exterior of either the transverse head section 40 or transverse feet section 42 for enhancing the ability of a user to reposition the acoustic and light therapy device, as desired. The wheels may further comprise spring casters for damping acoustic vibration to the environment exterior to the acoustic and light therapy device. It is generally desirable that the interior surfaces be comprised of pine, or a soft wood, to reduce echo and enhance quality of acoustic vibrations.

The above examples describes the use of "acoustic transducers", however for the purposes of the present description, the term "acoustic transducer" may refer to any general type of speaker, sound emitter, or sound driver. In the examples described, the term "sound" and "acoustic vibration" are used interchangeably.

While particular embodiments of the invention have been described and disclosed in the present application, it is clear that any number of permutations, modifications, or embodiments may be made without departing from the spirit and the scope of this invention. Accordingly, it is not the inventor's intention to limit this invention in this application, except as by the claims.

Particular terminology used when describing certain features or aspects of the invention should not be taken to imply that the terminology is being redefined herein to be restricted to any specific characteristics, features, or aspects of the invention with which that terminology is associated. In general, the terms used in the claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise embodiment or form disclosed herein or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference.

Aspects of the invention can be modified, if necessary, to employ the systems, functions, and concepts of the various references described above to provide yet further embodiments of the invention.

In general, the terms used in the claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention under the claims.

In light of the above "Detailed Description," Inventor may make changes to the invention. While the detailed description outlines possible embodiments of the invention and discloses the best mode contemplated, no matter how detailed the above appears in text, the invention may be practiced in a myriad of ways. Thus, implementation details may vary considerably while still being encompassed by the spirit of the invention as disclosed by the inventor. As discussed herein, specific terminology used when describing certain features or aspects of the invention should not be taken to imply that the terminology is being redefined herein to be restricted to any specific characteristics, features, or aspects of the invention with which that terminology is associated.

I claim:

1. An acoustic and light therapy device comprising:
a longitudinal center section comprising a center lower structure, a center upper structure, a transverse head section, and a transverse feet section, wherein said center lower structure comprises one or more acoustic transducers positioned along a longitudinal center plane and directed towards said center upper structure, wherein said center upper structure comprises one or more light fixtures positioned along said longitudinal center plane and directing light towards said center lower structure;
two longitudinal side sections, each comprising two longitudinal subsections, wherein each said longitudinal subsection comprises a side upper structure, a side lower structure, and a side wall thereby defining a longitudinal opening within a thickness of each said longitudinal subsection; and
wherein at least one of said longitudinal subsections is releasably adjoined substantially near a transverse center plane to another of said longitudinal subsections of one of said longitudinal side sections and hinged to said transverse head section or said transverse feet section.

2. The acoustic and light therapy device of claim 1, further comprising one or more comfort pads for enhancing user comfort and reducing rattling, wherein said one or more comfort pads are positioned directly above one or more of said center lower structure or one or more of said side lower structures.

3. The acoustic and light therapy device of claim 1, wherein one or more of said longitudinal side sections comprises an elliptical shape for enhancing acoustic vibration quality.

4. The acoustic and light therapy device of claim 1, wherein one or more of said one or more light fixtures is a polyhedral section comprising a plurality of mirrors for directing light towards one or more of said side lower structures or said center lower structure.

5. The acoustic and light therapy device of claim 1, wherein one or more of said longitudinal subsections further comprises one or more other acoustic transducers positioned on one of said side lower structures and directed towards one of said side upper structures.

6. The acoustic and light therapy device of claim 1, wherein one or more of said longitudinal subsections further comprises one or more other light fixtures positioned on one of said side upper structures and directed towards one of said side lower structures.

7. The acoustic and light therapy device of claim 1, further comprising at least one control knob for adjusting intensity of acoustic vibration.

8. The acoustic and light therapy device of claim 1, further comprising at least one control knob for adjusting intensity of light.

9. The acoustic and light therapy device of claim 1, further comprising at least one frequency selective control for adjusting intensity of acoustic vibration within a range of frequencies.

10. The acoustic and light therapy device of claim 1, wherein at least one of said longitudinal subsections are mirrored about said transverse center plane.

11. The acoustic and light therapy device of claim 1, wherein said center upper structure further comprises an ultraviolet emitter for disinfecting, wherein said ultraviolet emitter faces downward.

12. The acoustic and light therapy device of claim 1, wherein at least one of said one or more light fixtures further comprises a light filter for reducing electromagnetic radiation intensity in selective ranges.

13. The acoustic and light therapy device of claim 2, wherein said one or more comfort pads comprises a comfort pad center section and one or more comfort pad side sections as one component.

14. The acoustic and light therapy device of claim 4, wherein said polyhedral section is radially symmetric about a light fixture center.

15. The acoustic and light therapy device of claim 4, wherein at least one of said one or more light fixtures comprises a color distribution for enhancing comfort to a user.

16. The acoustic and light therapy device of claim 1, wherein at least one of said longitudinal side sections, transverse head section, or transverse feet section comprises pine.

* * * * *